United States Patent [19]

Bender et al.

[11] Patent Number: 4,869,983

[45] Date of Patent: Sep. 26, 1989

[54] SULFONYL-CONTAINING STYRENE DERIVATIVES AND THEIR USE IN ELECTROPHOTOGRAPHIC PROCESSES

[75] Inventors: Albert Bender, Nuremberg; Dieter Guenther, Kelkheim; Juergen Lingnau, Mainz-Laubenheim, all of Fed. Rep. of Germany

[73] Assignee: Hoechst Aktiengesellschaft, Frankfurt am Main, Fed. Rep. of Germany

[21] Appl. No.: 831,450

[22] Filed: Feb. 20, 1986

[30] Foreign Application Priority Data

Feb. 23, 1985 [DE] Fed. Rep. of Germany ....... 3506436

[51] Int. Cl.$^4$ .................. C07C 121/50; G03G 15/02; G03G 15/09
[52] U.S. Cl. ........................ 430/58; 430/83; 558/409
[58] Field of Search ................ 558/409; 430/58, 83

[56] References Cited

U.S. PATENT DOCUMENTS

| | | |
|---|---|---|
| 3,112,197 | 11/1963 | Neugebauer et al. ............... 96/1 |
| 3,180,729 | 4/1965 | Klupfel et al. ..................... 96/1 |
| 3,189,447 | 6/1965 | Neugebauer et al. ............... 96/1 |
| 3,257,203 | 6/1966 | Sues et al. ....................... 96/1.5 |
| 3,635,706 | 1/1972 | Kampfer et al. .................. 96/1.7 |
| 3,879,200 | 4/1975 | Regensburger et al. ........... 96/1.5 |
| 4,095,983 | 1/1978 | Wolff et al. ...................... 96/77 |
| 4,145,215 | 3/1979 | Van Allan et al. .................. 96/1 |
| 4,153,461 | 5/1979 | Berghaeuser et al. ............. 96/75 |
| 4,252,880 | 2/1981 | Lind et al. ........................ 430/82 |
| 4,278,747 | 7/1981 | Murayama et al. ................ 430/82 |
| 4,525,444 | 6/1985 | Doessel ........................... 430/96 |

FOREIGN PATENT DOCUMENTS 539930 12/1980 Australia ................... 96/1

3329442 3/1985 Fed. Rep. of Germany ........... 96/1

Primary Examiner—Mary C. Lee
Assistant Examiner—Robert C. Whittenbaugh
Attorney, Agent, or Firm—Foley & Lardner, Schwartz, Jeffery, Schwaab, Mack, Blumenthal & Evans

[57] ABSTRACT

Method and composition for a sulfonyl-containing styrene derivative of the general formula

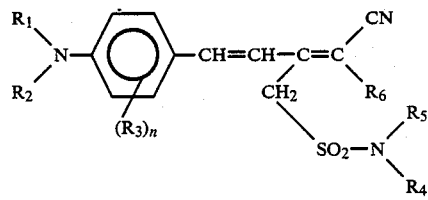

in which $R_1$ and $R_2$ are identical or different and denote hydrogen, optionally halogen-, hydroxyl-, cyano- or $(C_1-C_4)$-alkoxy mono- or poly-substituted $(C_1-C_8)$-alkyl or phenyl, $R_3$ denotes hydrogen or a $(C_1-C_4)$-alkyl or -alkoxy group, n is a number from 1 to 4 or $R_1$, $R_2$ and $R_3$ together with the associated aminophenyl radical denote julolidinyl or N-$(C_1-C_3)$-alkylcarbazol-3-yl, $R_4$ and $R_5$ denote hydrogen or the necessary valences for forming a condensation product with formamide derivatives, and $R_6$ denotes a cyano group, or $R_4$ denotes hydrogen and $R_5$ and $R_6$ together denote the grouping C=N—$R_7$, with $R_7$ being a benzoyl radical which is unsubstituted or substituted by $(C_1-C_4)$-alkyl or -alkoxy groups, halogen, cyno, amino or mono- or di-$(C_1-C_4)$-alkylamino groups, to a process for their preparation and to their use as dyes or in electrophotographic recording materials.

7 Claims, No Drawings

SULFONYL-CONTAINING STYRENE DERIVATIVES AND THEIR USE IN ELECTROPHOTOGRAPHIC PROCESSES

The present invention relates to new sulfonyl-containing styrenes, to a process for their preparation and to their use in electrophotographic recording materials.

The sulfonyl-containing styrenes according to the invention have the general formula I

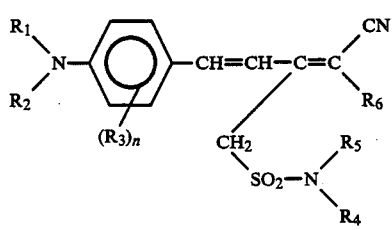

in which

R$_1$ and R$_2$ are identical or different and denote hydrogen, optionally halogen-, hydroxyl-, cyano- or (C$_1$-$_4$)-alkoxy-mono- or poly-substituted (C$_1$-C$_8$)-alkyl or phenyl, R$_3$ denotes hydrogen or a (C$_1$-C$_4$)-alkyl or -alkoxy group, n is a number from 1 to 4, or R$_1$, R$_2$ and R$_3$ together with the associated aminophenyl radical denote julolidinyl or N-(C$_1$-C$_3$)-alkylcarbazol-3-yl, R$_4$ and R$_5$ denote hydrogen or the necessary valences for forming a condensation product with formamide derivatives, and R$_6$ denotes a cyano group, or R$_4$ denotes hydrogen and R$_5$ and R$_6$ together denote the grouping $>C=N-R_7$ with R$_7$ as benzoyl which is substituted by (C$_1$-C$_4$)-alkyl or -alkoxy groups, halogen, cyano, amino or mono- or di-(C$_1$-C$_4$)-alkylamino groups.

Preference is given to compounds which are shown in the formula table (Table 6) as numbers II, III, IV and V in which R$_1$ denotes methyl, ethyl or ω-chloroethyl, R$_2$ denotes methyl or ethyl, R$_3$ denotes hydrogen or methoxyl, n denotes equal to 1 or R$_1$, R$_2$ and R$_3$ together with the associated aminophenyl radical denote julolidinyl, R$_4$ and R$_5$ denote hydrogen and R$_6$ denotes the cyano group or R$_4$ and R$_5$ together represent dimethylaminomethine or 4,6-dimethylpyridin-2-yl-aminomethine groups, or R$_4$ denotes hydrogen and R$_5$ and R$_6$ together denote the grouping C=N—R$_7$ and R$_7$ denotes a benzoyl radical which is unsubstituted or substituted by a methoxy or cyano group.

The compounds of the formula II according to the invention are formed by reaction of the ketosultams of the formula VI with malonic acid dnitrile of the formula VII, as depicted in reaction equation 1 (Table 7).

The invention also relates to a process for preparing the sulfonyl-containing styrenes according to the invention of the general formula I, which comprises reacting compounds of the general formula VI

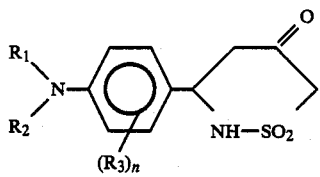

where R$_1$, R$_2$, R$_3$ and n have the meanings specified above with malonic acid dnitrile of the formula VII in an inert solvent at temperatures within the range from about 30° to about 150° C., isolating the resulting compounds of the general formula II by filtration and where applicable purifying by recrystallization.

DETAILED DESCRIPTION OF THE PREFERRED EMBODIMENTS

The reaction of the ketosultams of the formula with malonic acid dinitrile of the formula VII is carried out by heating the components in an inert solvent and if desired removing the resulting water of reaction from the reaction mixture by azeotropic distillation. Suitable solvents are alcohols such as methanol, ethanol, propanol and butanol, chlorinated hydrocarbons such as di-, tri- and tetrachloromethane, ethers such as diethyl ether, dioxane and tetrahydrofuran and aromatics such as benzene, toluene, xylenes and chlorobenzenes. Preferred solvents are benzene and toluene. The reaction temperature is within the range from about 30° to about 150° C., temperatures of from about 70° to about 100° C. being preferred. The compounds of the formula VI usually crystallize out of the reaction mixture. They can be isolated by filtration and purified in a conventional manner, such as, for example, by recrystallization. They are then obtained in the form of violet to deep blue crystals.

It was not foreseeable and therefore is very surprising that reaction of the uncolored ketosultams of the formula VI with malonic acid dinitrile of the formula VII in accordance with accompanying reaction equation 1 would produce dyes of the formula I which can be used for example as sensitizers for electrophotographic recording materials.

In a development of the invention, the sulfonyl-containing styrene derivatives of the formula II can be reacted at the sulfonamide group to give further dyes.

The modified process comprises reacting compounds of the general formula II with formamide acetals of the formula VIII (reaction equation 2) in an inert solvent at temperatures within the range of from about 65° to about .120° C., isolating the reaction product of the formula III, and purifying by recrystallization.

The R mentioned in the formula VIII of reaction equation 2 is selected from a C$_1$ or C$_2$ alkyl radical.

The reaction in accordance with equation 2 is carried out by heating the components in an inert solvent which preferably consists of methanol, ethanol, propanol, butanol or a mixture of alcohols. The reaction temperature is preferably at the boiling point of the respective solvent.

The compounds of the formula III according to the formula table usually crystallize out of the reaction mixture. They can be isolated by filtration and be purified by recrystallization. They are then obtained in the form of violet crystals.

In a further development of the invention, the sulfonyl-containing styrene derivatives of the formula II can undergo further modifications.

Such a process comprises reacting compounds of the general formula II with orthoformate esters of the formula IX and 2-amino-4,6-dialkylpyrimidine of the formula X in an inert solvent at temperatures within the range of from about 60° to about 140° C., isolating the reaction product and, where appropriate, purifying by recrystallization (reaction equation 3). The R in the formula IX of the reaction equation denotes a ($C_1$ or $C_2$)-alkyl radical.

The alkyl substituent on the pyrimidine of formula X is preferably methyl.

The compounds of formulas IX and X are known.

The reaction is carried out by heating the reactants in an inert solvent. Suitable solvents are alcohols such as methanol, ethanol, propanol and butanol, aromatics such as benzene, toluene, xylenes and chlorobenzenes or glacial acetic acid. A particular embodiment of the reaction comprises using the orthoformate ester of the formula IX both as reactant and as solvent. The reaction temperatures are between about 60° and about 140° C., preferably between about 80° and about 120° C. The compounds according to the invention of the formula IV usually crystallize out of the reaction mixture. They can be isolated by filtration and be purified by recrystallization. They are then obtained in the form of violet crystals.

In a further development of the invention the process for preparing the sulfonyl-containing styrene derivatives comprises reacting compounds of the general formula II in accordance with the reaction equation 4 with optionally substituted benzoyl chlorides of the formula XI in an inert solvent at temperatures within the range from about 30° to about 100° C., filtering off from undissolved matter, removing the solvent by distillation, and purifying the resulting reaction product by recrystallization.

The benzoyl chlorides of the formula XI, corresponding to benzoyl radicals $R_7$ as specified above, are known. The substituent R indicated in the reaction equation 4 has the meaning of hydrogen or independently of one another of one or more ($C_1$ to $C_4$)-alkyl or -alkoxy groups, halogen radicals such as fluorine, chlorine or bromine or cyano or amino, mono- or di-($C_1$ to $C_4$)-alkylamino groups.

The reaction is carried out by heating the reactants in an inert solvent. In this context, inert solvents include chlorinated hydrocarbons such as di-, tri- and tetra-chloromethane, ethers such as diethyl ether, diisopropyl ether, dioxane and tetrahydrofuran, and aromatics such as benzene, toluene, xylenes and chlorobenzenes. The reaction temperature is within the range between about 30° and about 100° C. It is advantageous to neutralize the hydrogen chloride formed in the course of the reaction with a base. The base can be inorganic, such as, for example, the hydroxides or oxides of alkali or alkaline earth metals, that is to say, for example, sodium hydroxide, potassium hydroxide, magnesium hydroxide, calcium hydroxide and the barium hydroxide or magnesium oxide or calcium oxide, or be organic such as alkylated amines, such as, for example, triethylamine, diisopropylamine, N,N-dimethylaniline or pyridine and lutidine.

The compounds according to the invention of the formula V usually remain dissolved in the reaction mixture. They are isolated by filtering off undissolved constituents and distilling off the solvent. After purification, such as, for example, by recrystallization, they are obtained in the form of red to violet crystals.

The ketosultam of the formula VI required for producing the sulfonyl-containing styrene derivatives prepared according to the invention is new and is the subject of a U.S. Patent Application filed on the same date under file reference 831,291.

The sulfonyl-containing styrene derivatives according to the invention can be used as dyes or in electrophotographic recording materials as sensitizers.

The generation of charge images on electrophotographic layers is effected after the charging by means of an exposure step. Exposure first generates an electric charge which in a further step is transported through the layer to the surface of the layer and neutralizes the charge present there. Here a distinction is made between photoreceptors where charge generation and charge transport are effected through the same chemical substance and those where the charge generation is obtained by addition of a second substance, the sensitizer. As a result it is possible to operate electrophotography even with light of a wavelength which is not absorbed by the actual photoconductive substance. The charge-transporting compounds which are used in the latter group of photoreceptors are usually organic donors, which are in some instances even part of a polymer molecule. Suitable for obtaining sensitization are not only colored pigments (for example known from U.S. Pat. No. 3,879,200) but also dissolved dyes. Particularly active disclosed dyes are said to be triphenylmethane dyes, such as, for example, brilliant green, C.I. 42 040 (U.S. Pat. No. 4,252,880), Rhodamine dyes, such as, for example, Rhodamine B, C.I. 45 140, and cyanine dyes such as Astrazone Orange R or G, C.I. 48 040 and 48 035 (German Offenlegungsschrift No. 2,949,826).

The low color fastness to be observed in the case of dyes which are dissolved in the polymer matrix does not permit use as sensitizers in cyclically working electrophotographic systems. The relatively low concentration required and the water solubility of these sensitizers, on the other hand, proves to be of advantage for use in eletrophotographic printing plates and printed circuits.

However, a disadvantage even with this type of use is the high preexposure sensitivity observed in these systems. If an electrophotographic photoreceptor which has been sensitized with soluble dyes of the type mentioned is accidentally exposed to light before the copying process, then after charging by means of a corona a highly reduced charge acceptance is observed in the previously exposed areas. This memory effect is removed only by storage for several hours.

In addition, the low solubility of the "soluble" dyes used, which are without exception cationic dyes, in the organic solvents used for the coating, such as tetrahydrofuran or esters, requires an additional processing step in which the dye is first predissolved in an alcohol and then added as a solution to the completed coating solution.

Finally, some of the previously used soluble sensitizing dyes, for example brilliant green, are substances whose use is not physiologically safe owing to their solubility in water. This necessitates special precautions in the handling of decoating solutions containing these dyes.

There was therefore the need for sensitizing dyes for electrophotography which are present in the polymer matrix solution and which do not have the disadvantages mentioned.

This need is met according to the invention with sulfonated styrene derivatives of the general formula I in which $R_1$ to $R_6$ and n have the above mentioned meaning.

These sensitizing dyes are added to the photoconductor layers of electrophotographic recording materials which comprise a conductive base material, where appropriate an insulating intermediate layer of low thickness and a photoconductive layer. The photoconductive layer can as a monolayer contain sensitizers and photoconductor in one layer, however, it can also comprise a charge-generating and a charge-transporting layer. In this case the charge-generating layer can contain the sensitizer(s), an electronically inert binder and where appropriate one or more organic pnhotoconductors, while the charge-transporting layer can be sensitizer-free and contain as essential layer constituents a photoconductor and binder. This organic photoconductor can as described in German Patent Application file reference P 33 29 442.9 also be introduced into the charge-generating layer by a diffusion process by using in the application of the charge-transporting layer a solvent in which the binder of the charge-generating layer is soluble or swellable.

Suitable electrically conductive base materials are materials having sufficient electrically conductive properties and being of the type which have also previously been used for this purpose. The base material can be present in the form of a flexible tape or a plate. In a preferred embodiment, the base material is suitable for the preparation of printing forms and printed circuits and comprises for example an aluminum, zinc, magnesium, copper, iron, nickel or a multimetal plate. It is also possible to use metallized, for example metal-vaporized, plastics films, such as aluminum-vaporized polyester films, or copper-laminated polyimide films and plates.

Surface-finished base materials made of aluminum are particularly suitable. The surface finish comprises a mechanical or electrochemical roughening and where appropriate a subsequent anodization and treatment with polyvinylphosphonic acid as described in U.S. Pat. No. 4,153,461.

Very generally, the insulating intermediate layer can be a barrier layer such as a thermally, anodically or chemically produced metal oxide layer, for example of aluminum oxide. The barrier layer has the function of reducing or preventing the injection of charge carriers from the electrically conductive base material in the dark into the layer which generates the charge carriers. The barrier layer also has a favorable effect on the adhesion of the subsequent layers to the base material. Organic barrier layers can be made of various natural or synthetic resin binders which adhere well to a metal or aluminum surface and do not undergo swelling or detatchment in the course of the subsequent application of further layers. The thickness of the organic barrier layer is of the order of 1 $\mu$m, and that of a metal oxide layer of the order of 10 to $10^4$ nm.

To prepare for example printed circuits of the type customary in electronics, the photoconductive double layer can also be first applied to an intermediate support, from where it is subsequently or later transferred as a so-called dry resist to the base material. This transfer can be effected for example by lamination. Particularly suitable intermediate supports are plastics films, such as those made of polyester, in particular polyethylene terephthalate film.

The sensitizing dyes used are according to the invention sulfonated styrene derivatives of the general formula I which where appropriate can also be used in mixture, also including sensitizing dyes of other classes of dye, for example in order to widen the sensitization spectrum. To obtain good sensitization properties it has been found to be suitable to add the dyes in concentrations between about 0.1 and about 5% by weight, preferably between about 0.25 and about 2% by weight, based on the weight of the photoconductor layer.

Suitable compounds for undertaking the charge transport in the charge transport layer are in particular those which have an extended $\pi$-electron system. They include monomeric heterocyclic compounds which are substituted by dialkyl-substituted amino groups or alkoxy groups. Suitable are in particular heterocyclic compounds such as oxadiazol derivatives which are mentioned in U.S. Pat. No. 3,189,447. These also include triphenylamine derivatives, oxazol, pyrazoline, triazole and imidazole derivatives, as reviewed for example in U.S. Pat. Nos. 3,257,203, 3,112,197 and 3,180,729. It is also possible to use hydrazone compounds of the type mentioned in U.S. Pat. No. 4,278,747. Preference is given to the use orf 2,5-bis-(4'-diethylaminophenyl)-1,3,4-oxadiazole, p-methoxybenzaldehydediphenylhydrazone and/or 1,5-diphenyl-3-p-methoxyphenylpyrazoline.

The highly insulating binders for the charge-generating layer and for the charge-transporting layer can be identical or different. Suitable flexibility, film-forming properties and adhesive strength properties are possessed by natural and synthetic resins which can be incipiently dissolved or swelled by customary solvents or solvent mixtures in the preparation of the layers. These include polyester resins which are copolyesters of isophthalic and terephthalic acid with glycols. Silicone resins have also been found to be suitable. Polycarbonate resins are highly usable. Particular preference for the preparation of printing forms and printed circuits is given to binders which are soluble in aqueous or alcoholic solvent systems, in the presence or absence of acid or alkali. Aromatic or aliphatic, highly flammable solvents are ruled out on physiological and safety grounds. Suitable resin binders are accordingly high-molecular substances which carry alkali-solubilizing groups. Examples thereof are acid anhydride, carboxyl, carboxamide, phenol, sulfo, sulfonamide or sulfonimide groups. It is preferred to use resin binders having high acid numbers. Copolymers with anhydride groups can be used highly successfully since as a consequence of the absence of free acid groups the dark conductivity is low, despite high alkali solubility. Particularly suitable are copolymers of styrene and maleic anhydride, sulfonyl urethanes as described in German Offenlegungsschrift No. 3,210,577 and copolymers of acrylic and methacrylic acid.

Customary additives present in the layers are substances which are added to the coating solution and as a result improve the surface structure and the flexibility. They can be for example plasticizers, such as triphenyl phosphate or flow-control agents, such as silicone oils.

The coatings are applied in a conventional manner, for example by knife-coating or spraying. The preferred method of application is flow-coating. The layers are dried for example in drying ducts where the various drying stages are fixed by the temperature of the individual zones, by the linear speed of the material and by the prevailing air flow.

EXAMPLES 1-7

The compounds of Examples 1 to 4 listed in Table 1, which have the formula II of the formula table, were prepared by the following, generally applicable method:

In each case 50 mmol of a compound of the formula VI, prepared in accordance with the German Application filed on the same date under file reference P 35 06 435.8 and 50 mmol of malonic acid dinitrile were heated in 100 ml of benzene with azeotropic removal of the water of reaction using a water separator. After the reaction had ended, the temperature was allowed to drop, the product was isolated by filtration and the filter residue was recrystallized from acetonitrile or glacial acetic acid.

The compounds of Examples 5 to 7 listed in Table 2, which have the formula III of the formula table, were prepared by the following, generally applicable method:

50 mmol of a compound of the examples mentioned in Table 1 and 60 mmol of dimethylformamide dimethyl acetal were stirred under reflux in 100 ml of isopropanol for 5 hours. After cooling, the product was filtered off and purified by crystallization from glacial acetic acid.

TABLE 1

| Example No. | $R_1$ | $R_2$ | $R_3$ | n | mp (°C.) | yield | $\lambda_{max}^{(DMF)}$ ($\epsilon$) |
|---|---|---|---|---|---|---|---|
| 1 | ω-chloroethyl | methyl | H | | 208-216 | 56% | 502 nm (15300) |
| 2 | methyl | methyl | 2-methyl-oxyl | 1 | 215-220 | 43% | 522 nm (19300) |
| 3 | ethyl | ethyl | H | | 212-216 | 38% | 525 nm (23400) |
| 4 | julolidinyl | | | | 227-231 | 47% | 557 nm (21200) |

TABLE 2

| Example No. | $R_1$ | $R_2$ | $R_3$ | mp (°C.) | yield | $\lambda_{max}^{(DMF)}$ ($\epsilon$) |
|---|---|---|---|---|---|---|
| 5 | ω-chloroethyl | methyl | H | 216-218 | 51% | 505 nm (27000) |
| 6 | ethyl | ethyl | H | 198-202 | 50% | 525 nm (46300) |
| 7 | julolidinyl | | | 241-243 | 33% | 559 nm (47600) |

EXAMPLE 8

17 g (50 mmol) of the compound of Example 3, 12.3 g (50 mmol) of 2-amino-4,6-dimethylpyrimidine and 50 ml of ethyl orthoformate were heated at 100° C. for 5 hours. After cooling, 20 g of crude product were isolated by filtration. Recrystallization left 9.1 g of a violet compound conforming to the formula IV of the formula table and having the following data:
mp 168°-171° C., yield 42%
$\lambda_{max}$(DMF)=530 nm, $\epsilon$=23,900.

EXAMPLES 9-13

Examples 9 to 13 of Table 3, which have the formula V of the formula table, were prepared by the following, generally applicable method:

50 mmol of a compound of the examples mentioned in Table 1 and 60 mmol of an appropriate benzoyl chloride were heated to 50° C. in 100 ml of tetrahydrofuran. 80 mmol of triethylamine were added dropwise. Six hours of reaction was followed by cooling down, removal of undissolved matter by filtration and evaporation of the solvent. The residue could be recrystallized from glacial acetic acid.

TABLE 3

| Example | $R_1$ | $R_2$ | $R_3$ | R | mp (°C.) | yield | $\lambda_{max}^{(DMF)}$ ($\epsilon$) |
|---|---|---|---|---|---|---|---|
| 9 | ω-chloroethyl | methyl | H | H | 202-204 | 54% | 482 nm (18700) |
| 10 | ethyl | ethyl | H | H | 224 | 42% | 507 nm (49200) |
| 11 | ethyl | ethyl | H | methoxyl | 222-224 | 40% | 501 nm (26300) |
| 12 | ethyl | ethyl | H | cyano | 240-243 | 72% | 509 nm (43300) |
| 13 | julolidinyl | | | H | 220-222 | 34% | 537 nm (45500) |

The compounds mentioned in Examples 1-13 gave the following values on elemental analysis:

TABLE 4

| Example No. | Empirical formula (molecular weight) | Calc. found | | C | H | N | S |
|---|---|---|---|---|---|---|---|
| 1 | $C_{16}H_{15}N_4O_2SCl$ (364.84) | | | 52.7 | 4.3 | 15.4 | 8.8 |
| | | | | 52.4 | 4.2 | 15.6 | 8.7 |
| | | Cl: | Calc. | 9.6 | found | 9.5 | |
| 2 | $C_{16}H_{18}N_4O_3S$ (346.52) | | | 55.5 | 5.2 | 16.2 | 9.2 |
| | | | | 55.4 | 5.3 | 16.2 | 9.1 |
| 3 | $C_{16}H_{20}N_4O_2S$ (344.43) | | | 59.4 | 5.9 | 16.3 | 9.3 |
| | | | | 59.0 | 5.9 | 16.0 | 9.6 |
| 4 | $C_{18}H_{20}N_4O_2S$ (368.42) | | | 62.8 | 5.4 | 15.2 | 8.7 |
| | | | | 62.7 | 5.3 | 15.2 | 8.8 |
| 5 | $C_{19}H_{22}N_5O_2SCl$ (419.30) | | | 54.4 | 5.3 | 16.7 | 7.6 |
| | | | | 54.1 | 5.2 | 16.9 | 7.5 |
| | | Cl: | Calc. | 8.4 | found | 8.6 | |
| 6 | $C_{20}H_{25}N_5O_2S$ (399.51) | | | 60.2 | 6.3 | 17.5 | 8.0 |
| | | | | 60.1 | 6.2 | 17.2 | 7.9 |
| 7 | $C_{22}H_{25}N_5O_2S$ (433.53) | | | 62.4 | 5.9 | 16.5 | 7.6 |
| | | | | 62.4 | 5.8 | 16.2 | 7.8 |
| 8 | $C_{24}H_{28}N_7O_2S$ (477.57) | | | 60.3 | 5.9 | 20.5 | 6.7 |
| | | | | 60.2 | 5.7 | 20.5 | 6.5 |
| 9 | $C_{23}H_{21}N_4O_3SCl$ (468.9) | | | 58.9 | 4.5 | 11.9 | 6.8 |
| | | | | 59.0 | 4.5 | 11.7 | 6.6 |
| | | Cl: | Calc. | 7.5 | found | 7.3 | |
| 10 | $C_{24}H_{24}N_4O_3S$ | | | 64.3 | 5.4 | 12.5 | 7.2 |

TABLE 4-continued

| Example No. | Empirical formula (molecular weight) | Calc. found | C | H | N | S |
|---|---|---|---|---|---|---|
| | (448.5) | | 64.3 | 5.4 | 12.3 | 7.7 |
| 11 | $C_{25}H_{26}N_4O_4S$ | | 62.7 | 5.5 | 11.7 | 6.7 |
| | (478.57) | | 62.8 | 5.5 | 11.5 | 6.4 |
| 12 | $C_{25}H_{23}N_5O_3S$ | | 63.4 | 4.9 | 14.8 | 6.8 |
| | (473.55) | | 63.2 | 4.8 | 14.6 | 6.5 |
| 13 | $C_{26}H_{24}N_4O_3S$ | | 66.1 | 5.1 | 11.9 | 6.8 |
| | (472.57) | | 66.3 | 5.2 | 12.0 | 6.6 |

EXAMPLES 14–25

In each case
0.5 g of the compounds of Tables 1 to 3,
50 g of 2,5-bis-(4-diethylaminophenyl)-1,3,4-oxadiazol and
50 g of the sulfonylurethane prepared by reaction of a polyvinyl butyral with—an equimolar amount based on free OH groups—propenyl sulfonyl isocyanate described in German Offenlegungsschrift No. 3,210,577, Example 1, were dissolved in
900 g of tetrahydrofuran.

After addition of 0.1 g of a silicone oil having a viscosity of 5 to 20 mPa.s this coating solution was applied to an electrochemically pretreated and anodized aluminum base as customarily used for preparing offset printing plates in such a way as to produce a dry coat weight of 6 g/m².

The presensitized electrophotographic printing plates thus prepared had electrophotographic properties reproduced in Table 5. They could be decoated by means of aqueous-alkaline decoating solutions. In a trial print a printing plate produced in this way gave an edition of far above 100,000 in good tone rendering.

EXAMPLE 26

0.5 g of a compound of Example 3 and
49.5 g of the sulfonyl urethane were dissolved in 450 g of tetrahydrofuran
and applied to an electrochemically pretreated and anodized aluminum base in such a way as to produce a coating weight of 3 g/m². This charge-generating layer had applied to it a charge-transporting layer comprising
25.0 g of 2,5-bis-(4-diethylaminophenyl)-1,3,4-oxadiazol,
25.0 g of sulfonyl urethane,
0.1 g of silicone oil and
450 g of tetrahydrofuran
in such a way that the total weight of the double coat was 6 g/m².

The electrophotographic data, like those of the following examples, can be found in Table 5.

EXAMPLE 27

Example 18 was repeated, except that instead of the sulfonyl urethane an alternating copolymer of styrene and maleic anhydride (decomposition point 200° to 240° C.) and instead of the 2,5-bis-(p-diethylaminophenyl)-1,3,4-oxadiazol 1,5-diphenyl-3-p-methoxyphenyl-pyrazoline (analogously to German Auslegeschrift No. 1,060,714) were used.

EXAMPLE 28

Example 18 was repeated, except that instead of the 2,5-bis-(p-diethylaminophenyl)-1,3,4-oxadiazol p-methoxybenzaldehydediphenylhydrazone as described in German Offenlegungsschrift No. 2,919,791 and instead of the sulfonyl urethane, a terpolymer of styrene, n-hexyl methacrylate and methacrylic acid in molar ratio of 10:60:30 were used.

EXAMPLE 29

Example 15 was repeated, except that the photoconductive layer was applied first to a polyethylene terephthalate film as an intermediate support and was transferred therefrom in a laminating step to a copper-laminated polyimide support.

EXAMPLE 10

(Comparative example)

Example 15 was repeated, except that instead of the dye of Example 3 Astrazone Orange R (C.I. 48 040) was used. This dye was dissolved in methanol before addition to the coating solution.

EXAMPLE 31

(Comparative example)

Example 15 was repeated, except that instead of the dye of Example 3 the laser dye No. 17 (U.S. Pat. No. 4,145,215) having the formula

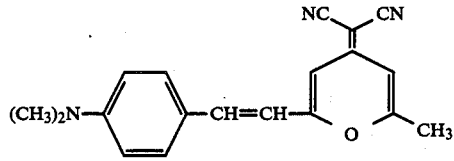

was used.

EXAMPLE 32

(Comparative example)

Example 30 was repeated, except that in addition to the Astrazone Orange the same amount of Rhodamine FB (C.I. 45 170) was additionally added to the layer.

The results of application Examples 1 to 32 are listed in Table 5 below. They reveal that recording materials incorporating the sulfonyl-containing styrene derivatives according to the invention combine good electrophotographic properties with satisfactorily low sensitivity to preexposure, which is of outstanding importance for industrial handling.

TABLE 5

| Example No. | Dye of Example No. | Charge Acceptance $U_{max}$ | Dark decay $U_{dark}$ (60″) | $E_{\frac{1}{2}+}$ | $U_o$ after exposure++ |
|---|---|---|---|---|---|
| 14 | 1 | −750 | −722 | 13.4 | −735 |
| 15 | 3 | −800 | −793 | 11.7 | −742 |
| 16 | 4 | −869 | −790 | 22.6 | −788 |
| 17 | 5 | −687 | −560 | 13.6 | −643 |
| 18 | 6 | −951 | −861 | 10.7 | −790 |
| 19 | 7 | −671 | −541 | 19.9 | −643 |
| 20 | 8 | −707 | −668 | 13.4 | −683 |
| 21 | 9 | −616 | −462 | 11.4 | −513 |
| 22 | 10 | −944 | −876 | 10.9 | −841 |
| 23 | 11 | −699 | −572 | 15.9 | −628 |
| 24 | 12 | −596 | −355 | 15.8 | −484 |
| 25 | 13 | −651 | −489 | 15.8 | −584 |
| 26 | 3 | −750 | −735 | 12.3 | −728 |
| 27 | 6 | −869 | −807 | 25.6 | −807 |
| 28 | 6 | −1007 | −935 | 17.1 | −734 |
| 29 | 3 | −755 | −754 | 10.9 | −734 |
| 30 (comp.) | — | −711 | −668 | 16.3 | −537 |
| 31 (comp.) | — | −742 | −699 | 24.6 | — |

TABLE 5-continued

| Example No. | Dye of Example No. | Charge Acceptance Umax | Dark decay $U_{dark}$ (60″) | $E_{\frac{1}{2}+}$ | $U_o$ after exposure++ |
|---|---|---|---|---|---|
| 32 (comp.) | — | −766 | −722 | 8.2 | −418 |

+necessary light energy for discharging the photoreceptor to half original charge, in μJ/cm² with a charge-up of −400 V and exposure with a halogen tungsten lamp using edge filters at 700 nm.
++maximum charge acceptance after exposure to fluorescent tubes (1000 lux) for 10 minutes.

TABLE 6
FORMULA TABLE

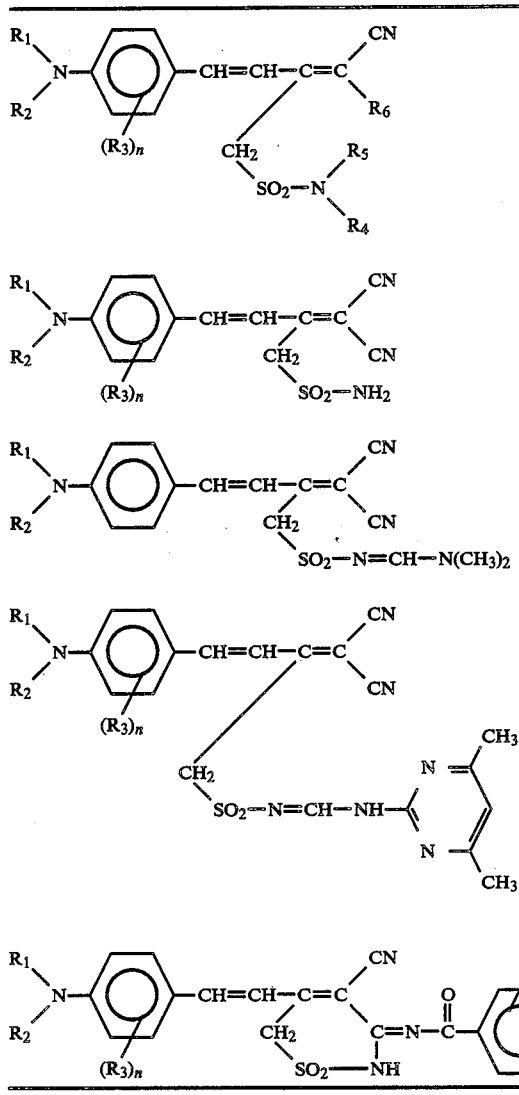

TABLE 7
REACTION EQUATIONS

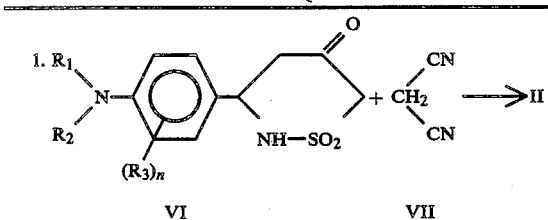

TABLE 7-continued
REACTION EQUATIONS

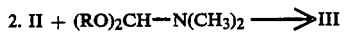

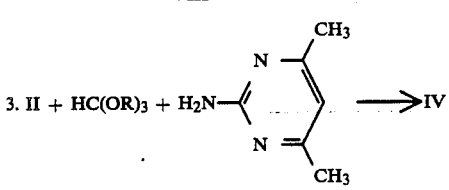

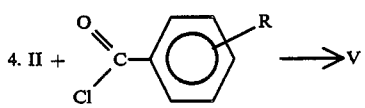

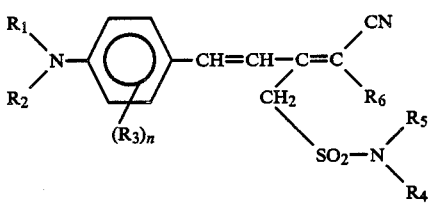

What is claimed is:

1. A sulfonyl-containing styrene derivative of the formula:

[Structure II]

wherein
$R_1$ and $R_2$ are the same or different and are selected from the group consisting of hydrogen, phenyl, $C_1$ to $C_8$ alkyl, and mono- and polysubstituted $C_1$ to $C_8$ alkyl, wherein the substitutions are the same or different and are selected from the group consisting of halogen, hydroxyl, cyano and $C_1$ to $C_4$ alkoxy,
$R_3$ is selected from the group consisting of hydrogen, a $C_1$ to $C_4$ alkyl and a $C_1$ to $C_4$ alkoxy,
n is a number from 1 to 4,
$R_4$ and $R_5$ are hydrogen or represent a dimethylaminomethine group, and
$R_6$ is a cyano group.

2. A styrene derivative as claimed in claim 1, wherein
$R_1$ is methyl, ethyl or ω-chloroethyl,
$R_2$ is methyl or ethyl,
$R_3$ is hydrogen or methoxyl,
n is 1 and
$R_4$ and $R_5$ are hydrogen.

3. A styrene derivative as claimed in claim 1, wherein $R_4$ and $R_5$ together represent a dimethylaminomethine group.

4. An electrophotographic recording material comprising a base material and a photoconductive layer which comprises a sensitizer comprising a sulfonyl-containing styrene derivative as claimed in claim 1.

5. An electrophotograhic recording material as claimed in claim 4, wherein said photoconductive layer comprises a charge-generating layer and a charge-transporting layer, said charge-generating layer comprising said sulfonyl-containing styrene derivative.

6. An electrophotographic recording material as claimed in claim 4, wherein said base material has a surface comprising aluminum, zinc, magnesium, copper, iron or nickel.

7. An electrophotographic recording material as claimed in claim 4, wherein said base material has a surface comprising a plastic film.

* * * * *